US009504458B2

(12) United States Patent
Obermiller et al.

(10) Patent No.: US 9,504,458 B2
(45) Date of Patent: Nov. 29, 2016

(54) METHODS AND SYSTEMS FOR TREATING COMPLEX FISTULAE

(71) Applicant: Cook Biotech Incorporated, West Lafayette, IN (US)

(72) Inventors: F. Joseph Obermiller, West Lafayette, IN (US); Kevin D. Parish, West Lafayette, IN (US); Mark Duncan, Westfield, IN (US); Derick C. Miller, Lafayette, IN (US); P. Arun Mohan, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 686 days.

(21) Appl. No.: 13/742,397

(22) Filed: Jan. 16, 2013

(65) Prior Publication Data

US 2013/0218201 A1 Aug. 22, 2013

Related U.S. Application Data

(60) Provisional application No. 61/600,124, filed on Feb. 17, 2012.

(51) Int. Cl.
*A61B 17/00* (2006.01)

(52) U.S. Cl.
CPC .. *A61B 17/0057* (2013.01); *A61B 2017/00606* (2013.01); *A61B 2017/00641* (2013.01); *A61B 2017/00663* (2013.01); *A61B 2017/00898* (2013.01)

(58) Field of Classification Search
CPC .............. A61B 17/0057; A61B 2017/00606; A61B 2017/00641; A61B 2017/00663; A61B 2017/00898
See application file for complete search history.

(56) References Cited

U.S. PATENT DOCUMENTS

| 4,511,653 A | 4/1985 | Play et al. |
| 4,902,508 A | 2/1990 | Badylak et al. |

(Continued)

FOREIGN PATENT DOCUMENTS

| WO | WO 98/22158 | 5/1998 |
| WO | WO 98/25637 | 6/1998 |
| WO | WO 2007/002260 A2 | 1/2007 |

OTHER PUBLICATIONS

Heeschen C., et al., "Nicotine stimulates angiogenesis and promotes tumor growth and atherosclerosis," Nature Medicine 7 (2001), No. 7, 833-839.

(Continued)

*Primary Examiner* — Ashley Fishback
(74) *Attorney, Agent, or Firm* — Woodard Emhardt Moriarty McNett & Henry LLP

(57) ABSTRACT

Described, in certain respects, are unique methods and systems for treating fistulae and other passageways and openings in the body. In some embodiments, treatment will be performed on fistulae that include a passage extending through a subcutaneous wall or wall-like structure. Illustratively, such a passage can extend through a subcutaneous tissue wall that includes, at a minimum, portions of an intestinal wall, and in this regard, such a wall can have a first side that is provided by the luminal side of the intestines and a second subcutaneous side that is provided, for example, by the abluminal side of the intestines and/or by other subcutaneous tissues adhered to this abluminal side. Some inventive products and methods involve sealing off the passage from both sides of the wall, for example, where a sealing element is placed on each side of the wall over an opening to the passage.

29 Claims, 7 Drawing Sheets

(56) References Cited

U.S. PATENT DOCUMENTS

| | | |
|---|---|---|
| 4,956,178 A | 9/1990 | Badylak et al. |
| 5,275,826 A | 1/1994 | Badylak et al. |
| 5,554,389 A | 9/1996 | Badylak et al. |
| 5,620,461 A | 4/1997 | Muijs Van De Moer |
| 5,993,844 A | 11/1999 | Abraham et al. |
| 6,099,567 A | 8/2000 | Badylak et al. |
| 6,206,931 B1 | 3/2001 | Cook et al. |
| 6,375,989 B1 | 4/2002 | Badylak et al. |
| 2007/0031508 A1* | 2/2007 | Armstrong et al. ......... 424/572 |
| 2009/0326577 A1 | 12/2009 | Johnson et al. |
| 2011/0060362 A1* | 3/2011 | Patel ............ A61B 17/0057 606/215 |
| 2013/0079811 A1* | 3/2013 | Agnew et al. ............. 606/213 |

OTHER PUBLICATIONS

Johnson C., et al., "Matrix Metalloproteinase-9 is Required for Adequate Angiogenic Revascularization of Ischemic Tissues: Potential Role in Capillary Branching," Circulation Research 94 (2004), No. 2, pp. 262-268.

\* cited by examiner

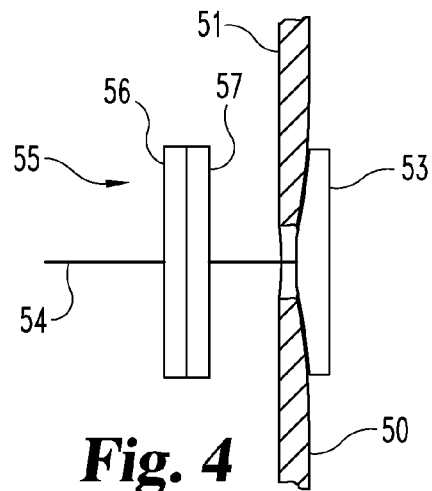
*Fig. 4*
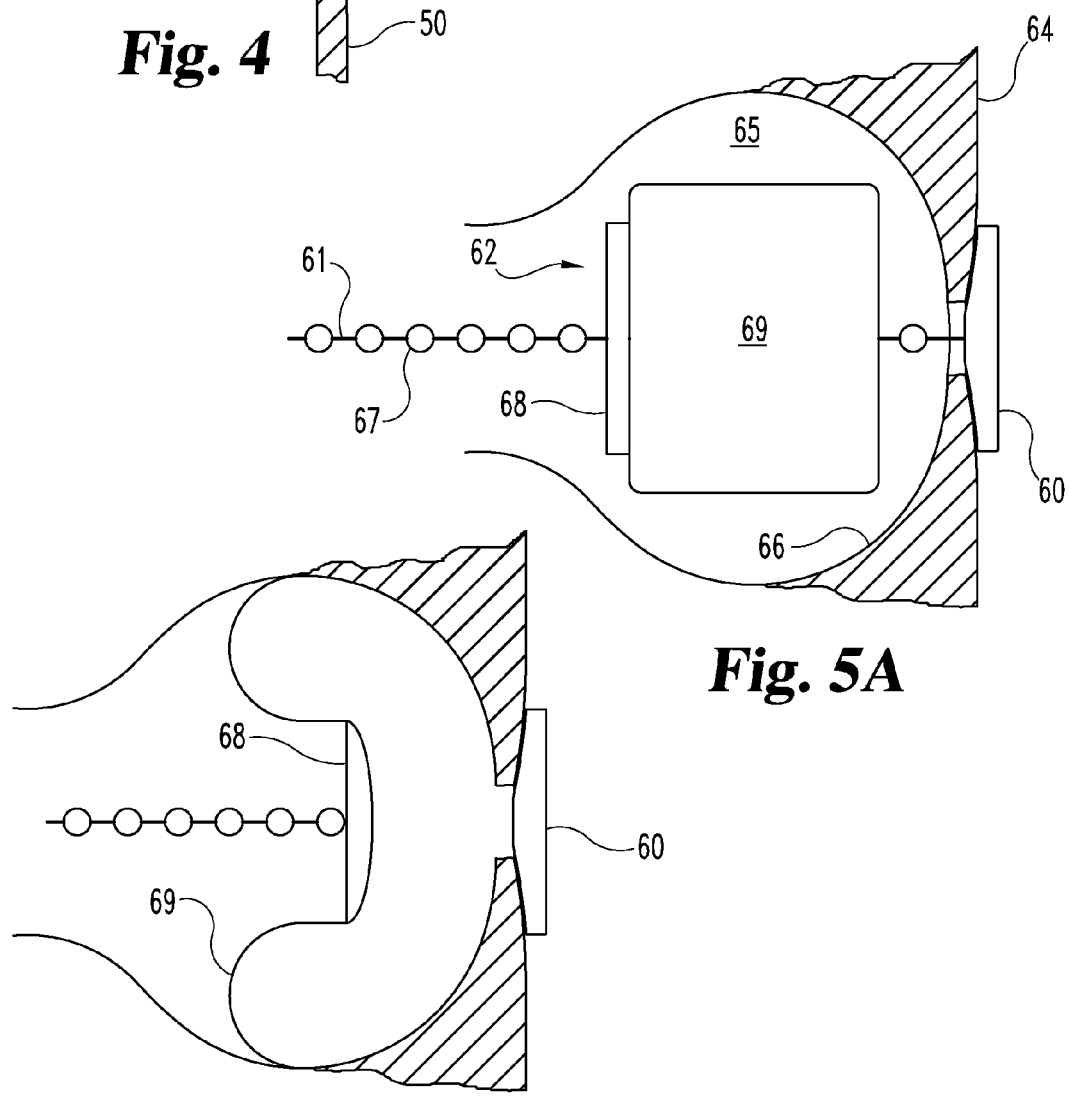
*Fig. 5A*
*Fig. 5B*

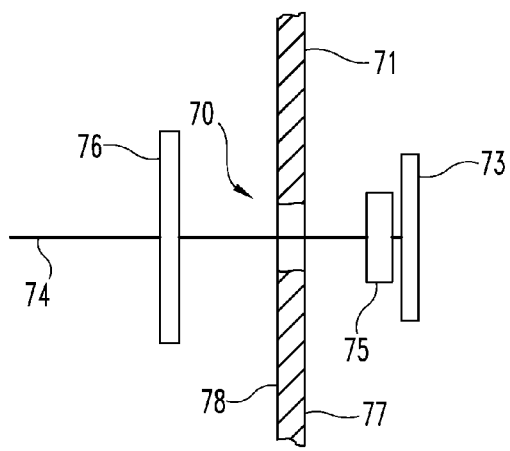
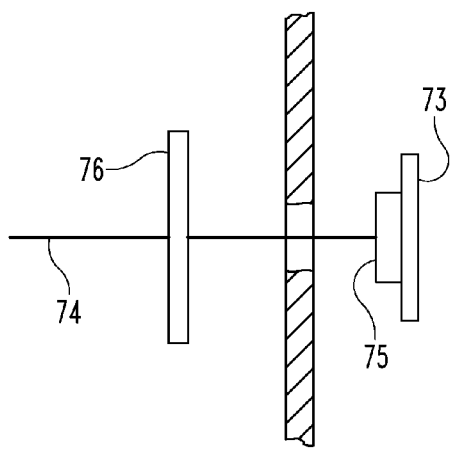
*Fig. 6A*  *Fig. 6B*
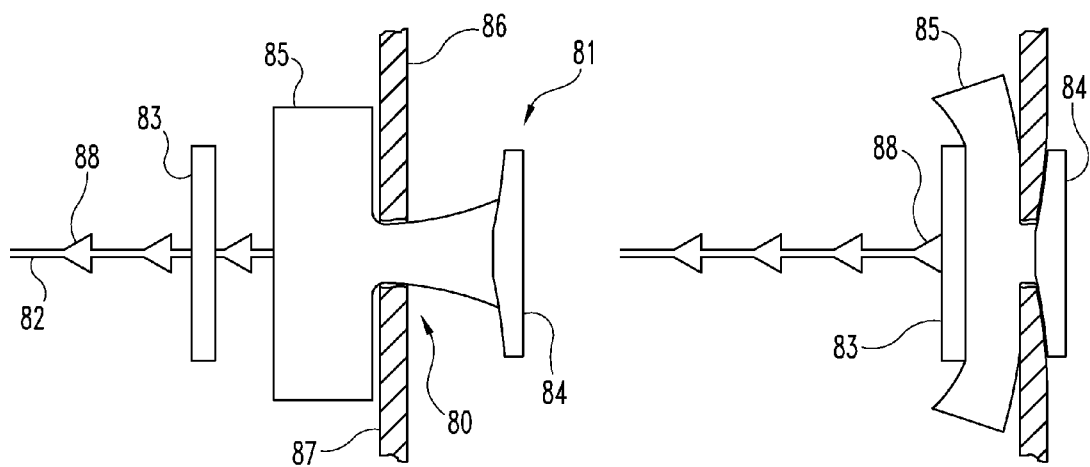
*Fig. 7A*  *Fig. 7B*

METHODS AND SYSTEMS FOR TREATING COMPLEX FISTULAE

REFERENCE TO RELATED APPLICATION

This application claims the benefit of U.S. Provisional Application No. 61/600,124, filed Feb. 17, 2012, which is hereby incorporated by reference.

BACKGROUND

The present invention relates generally to medical technology and in particular aspects to methods and systems for addressing fistulae and other passageways and openings in the body. As further background, there exist a variety of passageways and openings in the body which can be plugged, blocked or otherwise occupied by medical implants and materials to provide benefit to the patient. For example, it may be desirable to plug or otherwise treat a fistula. A variety of fistulae can occur in humans. These fistulae can occur for a variety of reasons, such as but not limited to, as a congenital defect, as a result of inflammatory bowel disease, such as Chron's disease, irradiation, trauma, such as childbirth, or as a side effect from a surgical procedure. Further, several different types of fistulae can occur, for example, urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae.

Anorectal fistulae can result from infection in the anal glands, which are located around the circumference of the distal anal canal that forms the anatomic landmark known as the dentate line. Approximately 20-40 such glands are found in humans. Infection in an anal gland can result in an abscess. This abscess then can track through soft tissues (e.g., through or around the sphincter muscles) into the perianal skin, where it drains either spontaneously or surgically. The resulting void through soft tissue is known as a fistula. The internal or inner opening of the fistula, usually located at or near the dentate line, is known as the primary opening. Any external or outer openings, which are usually located in the perianal skin, are known as secondary openings.

A gastrointestinal fistula is an abnormal passage that leaks contents of the stomach or the intestine (small or large bowel) to other organs, usually other parts of the intestine or the skin. For example, gastrojejunocolic fistulae include both enterocutaneous fistulae (those occurring between the skin surface and the intestine, namely the duodenum, the jejunum, and the ileum) and gastric fistulae (those occurring between the stomach and skin surface). Another type of fistula occurring in the gastrointestinal tract is an enteroenteral fistula, which refers to a fistula occurring between two parts of the intestine. Gastrointestinal fistulae can result in malnutrition and dehydration depending on their location in the gastrointestinal tract. They can also be a source of skin problems and infection. The majority of these types of fistulae are the result of surgery (e.g., bowel surgery), although sometimes they can develop spontaneously or from trauma, especially penetrating traumas such as stab wounds or gunshot wounds. Inflammatory processes, such as infection or inflammatory bowel disease (Crohn's disease), may also cause gastrointestinal fistulae. In fact, Crohn's disease is the most common primary bowel disease leading to enterocutaneous fistulae, and surgical treatment may be difficult because additional enterocutaneous fistulae develop in many of these patients postoperatively.

When surgery is deemed necessary, one operation for fistula closure is resection of the fistula-bearing segment and primary end-to-end anastamosis. The anastomosis may be reinforced by greater omentum or a serosal patch from adjacent small bowel. Still other methods for treating fistulae involve injecting sclerosant or sealant (e.g., collagen or fibrin glue) into the tract of the fistula to block the fistula. Closure of a fistula using a sealant is typically performed as a two-stage procedure, including a first-stage seton placement and injection of the fibrin glue several weeks later. This allows residual infection to resolve and to allow the fistula tract to "mature" prior to injecting a sealant. If sealant or sclerosant were injected as a one-stage procedure, into an "unprepared" or infected fistula, this may cause a flare-up of the infection and even further abscess formation.

There remain needs for improved and/or alternative devices and methods for addressing fistulae and other passageways and openings in the body. The present invention is addressed to those needs.

SUMMARY

The present invention provides, in certain aspects, unique methods and systems for treating fistulae and other passageways and openings in the body. Illustratively, some inventive methods are useful for blocking and in some cases substantially closing off fistulous passages that extend primarily through a wall of the alimentary canal such as where a passage exits the canal (e.g., the intestines) through an opening in the canal's luminal surface, and after traversing the canal wall, opens into a somewhat larger fistulous void adjacent the passage, for example, into an intraabdominal abscess that has formed to the abluminal side of the wall. In this regard, while some of these wholly-internal fistulous passages might only span up to the full thickness of the alimentary canal wall, others will traverse the wall and also adjacent tissues that have become undesirably adhered to the abluminal surface of the wall. In some preferred methods, steps will be taken to block off the passage from both directions, for example, including placing subcutaneous blocking elements along both sides of the canal wall over the respective openings. In a particularly preferred method, a first capping member will be arranged in a blocking position over an opening in the canal's luminal surface, and a second capping member will be arranged in a blocking position over an opening in the canal's abluminal surface. Such blocking positions can be effective to seal off or substantially seal off the passage, and in some instances, the canal wall will be compressed between the first and second capping members, for example, to give further integrity to the implanted product and/or the surrounding tissue for enhancing closure of the fistulous passage.

In one embodiment, an inventive product is useful for treating a fistulous passage that extends through a subcutaneous wall structure. This particular wall structure, while including tissue from at least a wall of the alimentary canal, has a first side that is provided by the luminal side of the alimentary canal wall and a second subcutaneous side that is opposite the first side. The fistulous passage extends from an opening in the first side of the subcutaneous wall structure to an opening in the second side of the subcutaneous wall structure. The product includes a first capping arrangement, a second capping arrangement and a guiding member. The first and second capping arrangements are deliverable to opposite sides of the subcutaneous wall structure for positioning over the first and second fistulous passage openings, respectively, with one or both capping arrangements optionally providing a filling material (e.g., a highly expandable material) in the fistulous passage. The guiding member can be made to extend from the first capping arrangement and to receive the second capping arrangement thereon so that, for example, when the first capping arrangement is in the alimentary canal (e.g., positioned over a primary fistula opening in a luminal surface of the canal), the guiding member can be made to extend through the fistulous passage and through the opening in the second side of the subcutaneous wall structure, and to potentially extend to a location outside the body. In this regard, with the second capping arrangement received on, around, etc. the guiding member, it can be delivered subcutaneously along the guiding member to the second side of the subcutaneous wall structure for positioning over the fistulous passage opening in the second side of the subcutaneous wall structure. The guiding member can exhibit a variety of shapes and configurations, for example, being a suture line or an elongate three-dimensional plug body capable of guiding the second capping arrangement to a treatment location. In some instances, the guiding member and the second capping arrangement will be specially cooperable with one another for generally maintaining a position of the second capping arrangement along the guiding member, e.g., in blocking position directly over the opening in the second side of the subcutaneous wall structure.

In another embodiment, the invention provides a medical product for treating a fistula having a primary opening in a wall of the alimentary canal and a secondary fistula opening in the skin (e.g., the perianal skin). This medical product comprises a first capping arrangement, a second capping arrangement and a guiding member. The first capping arrangement is deliverable to the alimentary canal and positionable over the primary fistula opening while providing a first filling material in the fistula. The guiding member extends from the first capping arrangement and is extendable through the fistula toward the secondary fistula opening when the first capping arrangement is positioned over the primary fistula opening. The second capping arrangement is received on, and is deliverable through the fistula along, the guiding member. In particular, the second capping arrangement is deliverable through the secondary fistula opening and toward the first capping arrangement when the first capping arrangement is positioned over the primary fistula opening for moving a second filling material toward the first filling material inside the fistula. In some forms, the first filling material and the second filling material will be sized and configured for contacting one another within the fistula proximate the primary fistula opening.

One aspect of the present invention provides a method for treating a fistula having a primary opening in a wall of the alimentary canal and a secondary fistula opening in the skin. This method includes delivering a first capping arrangement to the alimentary canal so that it is positioned over the primary fistula opening and provides a first filling material within the fistula. Additionally, a guiding member is made to extend from the first capping arrangement and through the fistula toward the secondary fistula opening when the first capping arrangement is positioned over or around the primary fistula opening. In some instances, the guiding member will be part of the first capping arrangement. In a further step, a second capping arrangement is delivered through the secondary fistula opening and along the guiding member so that it advances through the fistula toward the first capping arrangement. The second capping arrangement can be advanced to the point of contacting the filling material of the first capping arrangement, and in some cases, this contact will be effective to somewhat compress the first filling material inside the fistula. In a particularly preferred form, the second capping arrangement will include its own filling material and advancing the second capping arrangement through the fistula will be effective to bring this second filling material into contact with the filling material of the first capping arrangement, e.g., in and/or around the primary fistula opening.

Another aspect of the invention provides a medical product for treating a fistula having a primary opening in a wall of the alimentary canal and a secondary fistula opening in the skin. This medical product comprises a first capping arrangement that includes a first support element associated with a first filling material. The first capping arrangement is deliverable to the alimentary canal for positioning over the primary fistula opening with the first support element supporting the first filling material in a blocking position over the primary fistula opening. This medical product also includes a guiding member that can be made to extend from the first capping arrangement and through the fistula toward the secondary fistula opening when the first capping arrangement is positioned over the primary fistula opening. This medical product also comprises a second capping arrangement that includes a second support element and a second filling material. The second capping arrangement, which is receivable on the guiding member, is deliverable along the guiding member and through the secondary fistula opening toward the first capping arrangement when the first capping arrangement is positioned over the primary fistula opening. The first support element can incorporate a frame element such as a resilient wire support frame supporting a deformable covering material.

Other objects, embodiments, forms, features, advantages, aspects, and benefits of the present disclosure shall become apparent from the detailed description and drawings included herein.

BRIEF DESCRIPTION OF THE DRAWINGS

FIG. 4 shows a side view of an inventive medical product at a treatment site.

FIG. 5A shows a side view of an inventive medical product at a treatment site.

FIG. 5B shows a further condition of the medical product of FIG. 5A at the treatment site.

FIG. 6A shows a side view of an inventive medical product at a treatment site.

FIG. 6B shows another inventive medical product at a treatment site.

FIG. 7A shows still another inventive medical product at a treatment site.

FIG. 7B shows the medical product of FIG. 7A in a further condition at the treatment site.

DETAILED DESCRIPTION

Figure 1:
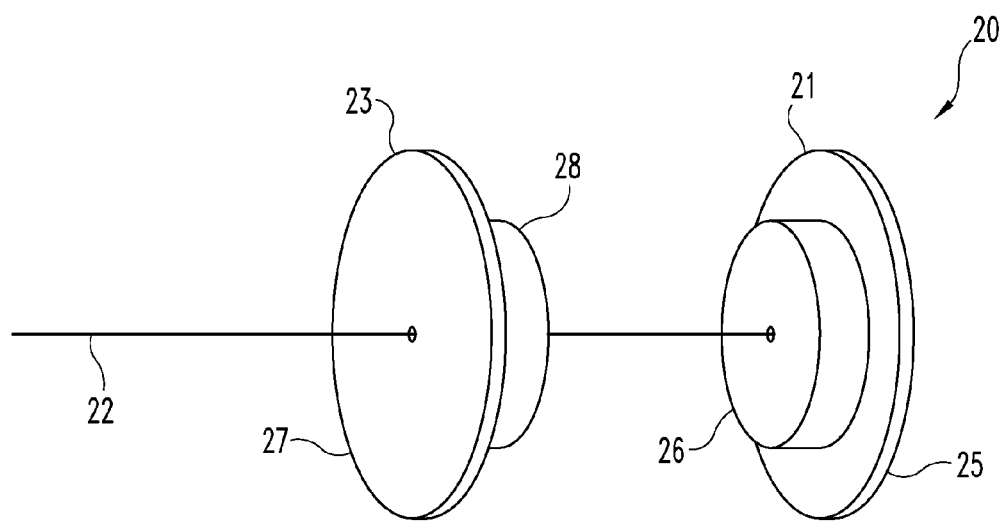
FIG. 1 is a perspective view of medical product according to one embodiment of the present invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique methods and systems for treating fistulae and other passageways and openings in the body. In some respects, the present disclosure describes unique solutions for treating fistulae that have a primary opening in a wall of the alimentary canal or in a wall of another bodily organ or vessel as described elsewhere herein. Such fistulae, in some instances, will include a fistulous passage that extends from the primary opening to a second subcutaneous opening. For example, a fistulous passage can extend through a subcutaneous wall structure that includes, at a minimum, portions of the alimentary canal wall. Such a wall or wall-like structure can have a first side that is provided by the luminal side of the alimentary canal wall and a second subcutaneous side that is opposite the first side, and in this regard, the second side might at least in part be provided by the abluminal side of the alimentary canal wall. Additionally or alternatively, the second side might at least in part be provided by subcutaneous layers that are lying adjacent to (e.g., have become adhered to) the abluminal side of the alimentary canal wall.

In some preferred aspects, the invention provides products and methods that will enable blocking of the fistulous passage at subcutaneous locations from both sides of the subcutaneous wall structure, for example, where opposing blocking elements are configured for placement against opposite sides of the subcutaneous wall structure and over the respective subcutaneous fistula openings. In some embodiments, an inventive system will include a first capping arrangement that is deliverable to the first side of the subcutaneous wall structure for assuming a blocking position over the primary fistula opening, and a second capping arrangement will be deliverable to the second side of the subcutaneous wall structure for assuming a blocking position over the second subcutaneous fistula opening. Optionally, such a system will further include some sort of a guiding member that can be made to extend from the first capping arrangement for receiving the second capping arrangement thereon so that, for example, when the first capping arrangement is in the alimentary canal (e.g., positioned over the primary fistula opening), the guiding member can be made to extend through the fistulous passage and through the second subcutaneous fistula opening. Preferably, the guiding member will continue to extend from there through further subcutaneous tissues until it exits the fistula altogether, for example, through an opening in the patient's skin. In this regard, with the second capping arrangement received on, around, etc. the guiding member, the second capping arrangement can be delivered through the skin-side opening and through subcutaneous tissues along the guiding member until it reaches the second side of the subcutaneous wall structure for positioning over the second subcutaneous fistula opening. The invention further provides methods for preparing these and other treatment devices, as well as medical products that include such treatment devices enclosed within sterile packaging.

With reference now to FIG. 1, shown is a medical product 20 according to one embodiment of the present invention. Product 20 includes a first capping arrangement 21, a guiding member 22 that extends from the first capping arrangement, and a second capping arrangement 23 that is received on and translatable along the guiding member. First capping arrangement 21 incorporates a generally disc-shaped first support element 25 that is supportive of a generally cylindrical first filling material 26, while second capping arrangement 23 incorporates a similar second support element 27 that is supportive of a second filling material 28. Such a medical product can be used in the treatment of a variety passageways and openings in the body including fistulae. For example, whether delivered contemporaneously or not, the respective capping arrangements can be placed on opposite sides of a subcutaneous wall structure for blocking, and in some cases substantially sealing off, an opening or passage (e.g., a fistulous passage) that extends into or through the subcutaneous wall structure. This sort of blocking system can utilize a variety of different opposable cap or cap-like members (with optional filling materials) including those described herein.

Any portion of a capping arrangement (e.g., a backing member, filling material, frame element, etc.) can be formed with one or more of a variety of biodegradable and/or non-biodegradable materials including those described herein. When a capping element relies, at least in part, on its size and shape to inhibit it passage through a bodily opening or passageway, this sort of element can be shaped and configured in a variety of manners. Suitable shapes include but are not limited to various three-dimensional shapes having rectilinear and/or curvilinear features. Suitable three-dimensional rectilinear shapes can have any suitable number of sides, and can include, for example, cubes, cuboids, tetrahedrons, prisms, pyramids, wedges, and variations thereof. Suitable three-dimensional curvilinear shapes can include, for example, spheres, spheroids, ellipsoids, cylinders, cones, and any suitable variations thereof (e.g., a segment of a sphere, or a truncated cone, etc.). When adapted for positioning over an opening in a tissue wall, a capping arrangement, or any element thereof, can be sized for contacting portions of the tissue wall adjacent the opening so as to inhibit its passage into or through the opening.

Continuing with FIG. 1, in one preferred method for treating a fistula that has a primary opening in the alimentary canal, the first capping arrangement 21 can be delivered into the canal so that it is generally positioned over the primary fistula opening. This can be done so that the first filling material 26 is generally facing the primary opening with the first support element 25 contacting tissues around the opening and providing support to the first filling material 26, for example, so as to eventually help maintain the filling material in a blocking, closing, sealing, etc. position in and/or over the primary fistula opening. Delivery of the first capping arrangement 31 to the primary opening can be accomplished in any suitable manner including, for example, by delivering the arrangement through the canal from another bodily location (e.g., from the mouth), or by passing the arrangement through the fistula itself from a secondary opening in the skin. While not necessary, in some instances, the capping arrangement will be made compressible or otherwise deformable, for example, so that it can be folded, rolled, collapsed and/or otherwise compacted to a lower-profile condition (e.g., for placement in a delivery device) for traversing a passageway en route to the primary opening.

With the first capping arrangement 21 positioned over the primary opening, the guiding member 22 can extend from it and through the fistula, potentially exiting the skin. In some cases, maintaining the capping arrangement in place over the opening will be accomplished, at least in part, by applying tension to guiding member 22 and maintaining this tension. Additionally or alternatively, the capping arrangement, or any element thereof such as backing member, can be bonded or otherwise attached to tissue around the opening, and in some forms, incorporate barbs or other adaptations to penetrate into tissue around the fistula to at least help hold the capping member in place. With the first capping arrangement 21 desirably positioned, the second capping arrangement 23 can be advanced into the fistula along the guiding member 22. This can be done as shown in FIG. 1 with the second filling material 28 generally facing the first filling material 26. In some cases, the opposing fill materials will contact one another in the fistula, for example, in and/or around the primary fistula opening. When advanced to a suitable location along the guiding member 22, the second capping arrangement 23 can be generally fixed in place along the guiding member in a variety of manners, for example, as discussed herein below.

While suture material, in particular, will be useful in certain inventive embodiments as the guiding member, as discussed elsewhere herein, a variety of other elongate materials and objects capable of extending within a fistula or other bodily passageway can be used as an alternative to, or in addition, to suture material. These include various biodegradable and non-biodegradable cords, filaments, chains, strings, elongate graft members, wires and other similar objects having relatively slender profiles for extending through a fistula tract or other passageway or void in patient tissue. In some instances, a somewhat heftier elongate structure such as a generally solid biodegradable or non-biodegradable three-dimensional graft body will be made to extend through a bodily opening or passageway. Such a structure will generally have more heft and bulk than a conventional thread or filament.

Capping arrangements can be or include a variety of different frame and frame-like elements. These include single- and multiple-part devices. In some forms, a frame member will include a filament or wire body or other similar frame or frame-like support structure. Frame members, in some embodiments, can be designed to move between a first condition and one or more other conditions, for example, in the case of a frame that is compactable to a compacted, first condition, and when in this compacted condition, is then expandable to an expanded, second condition. In forms where a frame has the capacity to expand, these frames can include those that are considered self-expanding and those that require at least some manipulation in order to expand. Frames of this sort and other similar support elements useful in the present invention can be constructed using one or more pieces of superelastic wire or any of a variety of other suitable materials described herein or otherwise known to those skilled in the art including MRI compatible materials. Frames and other similar expandable and non-expandable support members, when utilized in the present invention, may be made from metallic or non-metallic material, or both. The non-metallic material can suitably be a synthetic polymeric material, including for example bioresorbable and/or non-bioresorbable plastics. Materials commonly used in medical device construction include biologically compatible metals, e.g., stainless steel, titanium, tantalum, gold, platinum, copper and the like, as well as alloys of these metals; synthetic polymeric materials; low shape memory plastic; a shape-memory plastic or alloy, such as nitinol; and the like.

Figure 2:
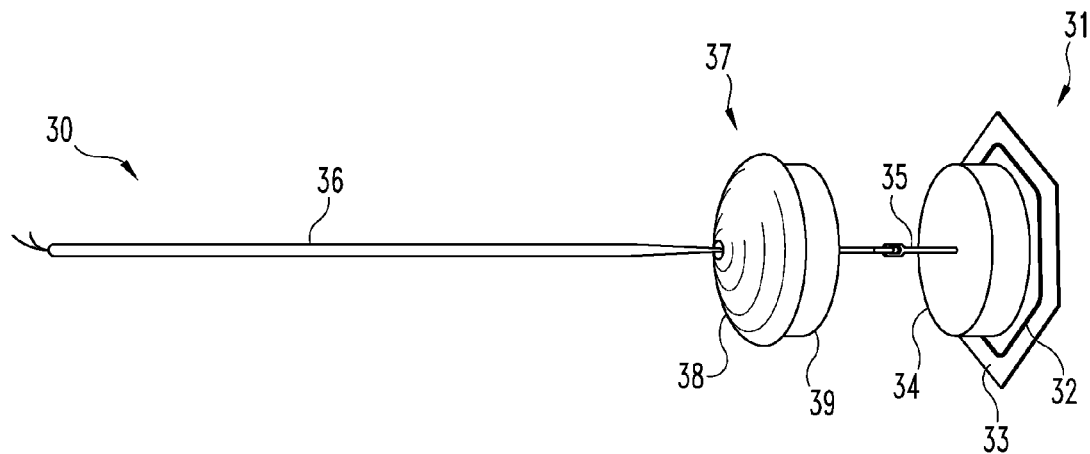
FIG. 2 is a perspective view of another inventive medical product.

With reference now to FIG. 2, shown is a medical product 30 according to another embodiment of the present invention. Product 30 includes a first capping arrangement 31 which includes a generally hexagonal, resilient wire frame member 32 that is supportive of a deformable covering material 33. A generally cylindrical, first filling material 34 is attached to the covering material and is positioned to the interior of the hexagonal frame. The first capping arrangement further provides a connecting pin 35 that is retained in association with the covering material and extends through the filling material for connecting the first capping arrangement to an elongate tether 36. A second capping arrangement 37, which is received over and translatable along the tether as shown in FIG. 2, includes a slightly dome-shaped backing member 38 and a generally cylindrical, second filling material 39.

Figure 3:
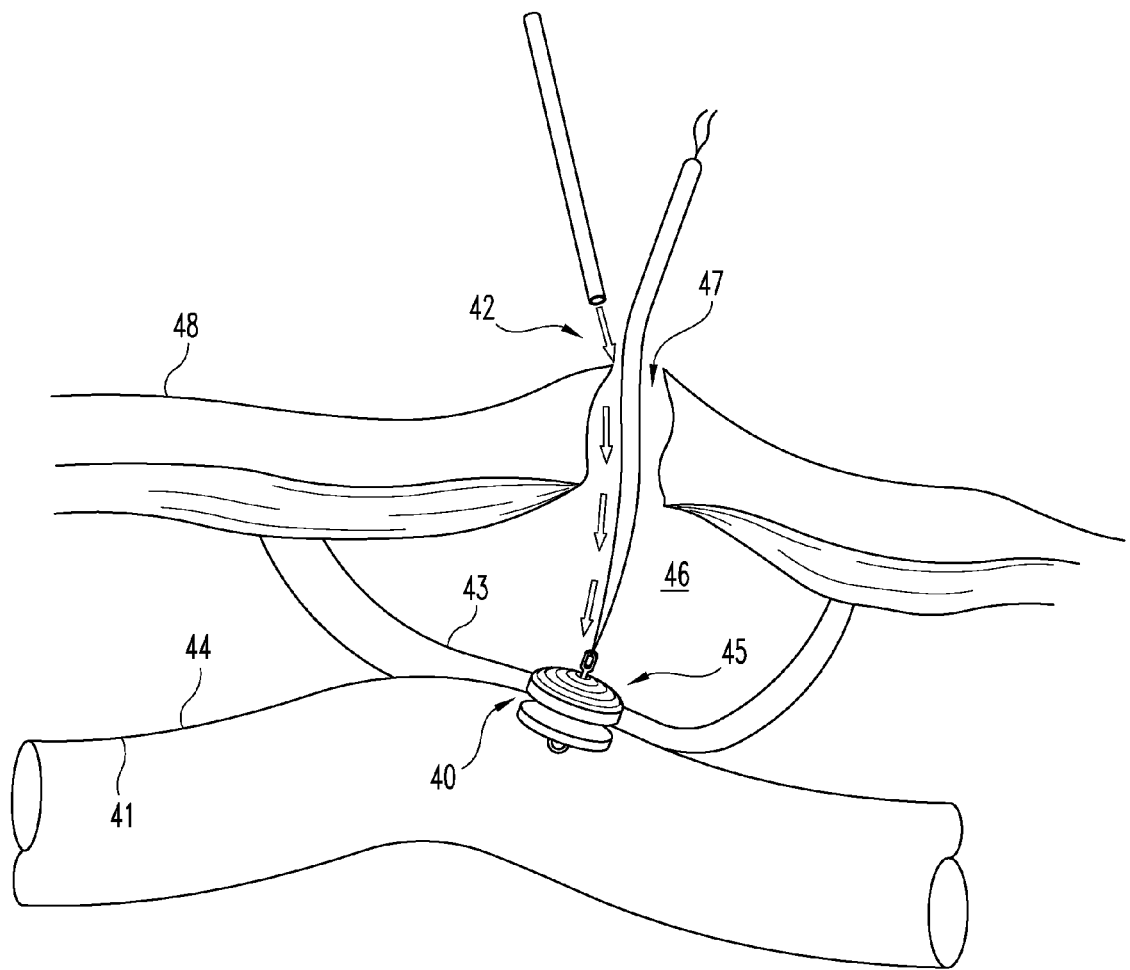
FIG. 3 shows an inventive medical product implanted in a patient.

A medical product of this sort can be used to treat a variety of fistulae and other passageways and openings in the body. In some respects, such products will be used to treat gastrointestinal or other fistulae that have a primary opening in an intestinal or stomach wall. FIG. 3 shows an enterocutaneous fistula having a primary opening 40 in an intestinal wall 41, and is merely illustrative of one type of abnormality that can be treated using medical product 30. It should be well understood that no two fistulae are identical. Even fistulae of the same general type can be quite diverse in terms of their size, shape, length, starting location(s), ending location(s), complexity, the types of tissues they involve, and potentially many other respects.

Continuing with FIG. 3, primary fistula opening 40 leads out of the intestines and ultimately to a skin-side fistula opening 42. In doing so, the fistula passes through various subcutaneous tissues including intestinal wall 41 and some abdominal, peritoneal or other tissues 43 that have become undesirably adhered to the abluminal side 44 of the intestinal wall. A fully-internal fistulous passage (blocked from view in this illustration by medical product 30) extends through these adjoining subcutaneous tissues, i.e., from primary opening 40 to a second subcutaneous opening 45. This second subcutaneous opening 45 opens into a somewhat larger cavernous region 46 which may be associated with an abscess. Closer to the skin, this cavernous region leads to a fistula tract 47. This fistula tract 47 continues through the outermost abdominal layers and the skin 48, and provides an open passage to the outside of the patient's body through skin-side opening 42. While the arrangement and relative sizes of the bodily features shown in FIG. 3 certainly embody those of an enterocutaneous fistula that can be treated using medical products of the invention, again, it should be understood that they merely represent one possible layout of an enterocutaneous fistula. In some instances, the size and shape of the cavernous region will be different than what is shown in FIG. 3, or there will be no cavernous region, or the cavernous region will not be readily discernable from a fistula tract leading to the skin.

Continuing with FIG. 3, in this treatment scenario, first capping arrangement 31 is shown at least partially in the alimentary canal and positioned over primary fistula opening

40 such that the first filling material 34 is facing the primary opening for blocking, closing, sealing off, etc. the primary opening, optionally with all or a portion of the first filling material 34 extending into or residing within the primary opening 40. Desirably, the hexagonal frame member 32 will be of sufficient size to surround the primary fistula opening on the luminal side of the alimentary canal wall. This will at least help anchor the first capping arrangement in the alimentary canal and prevent it from being pulled completely through the primary opening, for example, in cases where considerable pulling forces are applied to tether 36 for holding the first capping arrangement over the primary opening. Frame member 32 also provides support to the deformable covering material 33 which can be effective to cover and in some cases substantially seal off the primary opening, for example, where interior portions of the covering are pulled through the opening as discussed elsewhere herein. Delivery of the first capping arrangement 31 into the alimentary canal can be accomplished in any suitable manner including, for example, by compressing it within a sheath and passing it directly through the fistula from skin-side opening 42.

With the first capping arrangement 31 positioned over the primary opening, tether 36 extends from pin 35, through cavernous region 46 and through fistula tract 47 until it exits the fistula through skin-side opening 42. Second capping arrangement 37 is received over tether 36 and resides deep within the fistula over second subcutaneous opening 45 such that second filling material 39 is facing the second subcutaneous opening for blocking, closing, sealing off, etc. the second subcutaneous opening, optionally with all or a portion of the second filling material 39 extending into or residing within the second subcutaneous opening 45. Delivery of the second capping arrangement 37 to this location can be accomplished in any suitable manner including by advancing the arrangement through the skin-side opening 42 over tether 36 after the first capping arrangement 31 has been deployed. Alternatively, the second capping arrangement 37 can be pre-loaded over tether 36 and both capping arrangements can be delivered into the fistula contemporaneously inside a delivery sheath. Backing member 38 is supportive of second filling material 39 in and/or around the second subcutaneous opening 45. In some preferred instances, the opposing filling materials will contact one another in the fistula, for example, with the first filling material 34 residing in the primary fistula opening 40 and with the second filling material 39 residing in the second subcutaneous opening 45 so that the two fill material come together in the fistulous passage that extends between these two subcutaneous openings. When advanced to a suitable location along tether 36, the second capping arrangement 37 can be generally fixed in place along tether 36, for example, to maintain the opposing filling materials in a contacting, and in some cases, a compressed condition with the intestinal wall and other subcutaneous tissues squeezed between the opposing capping arrangements.

Optionally, once the dual capping arrangements are desirably located in the body, one or more back-fill materials, members, etc. can be delivered into the fistula, for example, to occupy portions of the cavernous region 46 and/or fistula tract 47. The arrows in FIG. 3 show how a backfilling, elongate plug member 49 can be delivered into the fistula alongside tether 36. Multiple such members can be located in the fistula. These and/or other fillers can be or include a variety of biodegradable and/or non-biodegradable objects and materials including flowable and non-flowable materials and objects. In some instances, the tether will aid in the delivery of a fill substance into the fistula such as where a three-dimensional plug or plug-type device, or a separate delivery instrument carrying such a device, is specifically adapted to track along the line inside the fistula. Suitable fill substances for this and other embodiments disclosed herein include various space filling materials such as remodelable or resorbable materials, for example, a comminuted, fluidized, and/or gelatinous remodelable material as described elsewhere herein, or other substances (e.g., in the form of fluids, pastes, gels, sponges, powders, tissue fragments, segments, strips, layers, etc.), therapeutic agents, e.g. suitable drugs such as antibiotics, antimicrobial agents or the like. Other options include but are not limited to polymer, contrast medium, saline, a non-bioabsorbable material, collagen rods or particulates, a collagenous or gelatinous foam, chitosan, gelatin, oxidized regenerated cellulose, calcium alginate, alginate, thrombin-fibrin enhanced materials, fibrin glues, or any suitable combination thereof. As well, a plug or other material might be coated with one or more substances such as a drug coating, adhesive, sclerosant or the like.

FIG. 4 shows an inventive treatment system for blocking a fistulous opening or passage that extends through a subcutaneous wall of tissue. In some preferred treatment scenarios, a first side 50 of the tissue wall is provided by a luminal side of a patient's stomach or intestines, and a second side 51 is underneath the skin and opposite the first side. In some instances, this second side 51 is primarily the abluminal side of the stomach or intestines. In other instances, the wall's second side 51 will be provided at least in part by other subcutaneous tissues or structures, for example, where abdominal, peritoneal or other tissues have undesirably adhered to the abluminal surface of the stomach or intestines to form a sort of wall or wall-like structure with a fistulous opening or passage extending through the wall.

Continuing with FIG. 4, the treatment system includes a first capping arrangement 53, a guiding member 54 and a second capping arrangement 55. First capping arrangement 53 is positioned against the first side 50 of the tissue wall and over the fistulous opening or passage. First capping arrangement 53 could be any of the cap or cap-like arrangements disclosed herein and in this regard it will be understood that the various disclosed capping elements are interchangeable to the extent practicable. This particular capping arrangement is shown convexly shaped and extending somewhat into the fistulous opening or passage for providing enhanced closure of the opening or passage from the stomach or intestinal side. Such a capping arrangement can be manufactured to already have somewhat of a convex shape, or it can be deformable at the treatment site into a deformed condition exhibiting a generally convex shape. Guiding member 54, which is connected to the first capping arrangement, passes through the fistulous opening or passage and extends to a location away from the fistulous opening or passage, e.g., to a location outside the patient's skin. Second capping arrangement 55, which includes a backing member 56 adjacent a filling material 57, is received over the guiding member for advancement toward the first capping arrangement inside the body. The backing member and filing material may or may not be attached to one another. In some preferred forms, the second capping arrangement will be advanced until the filling material 57 rests against the wall's second side 51 over a fistulous opening, for example, where the filling material fully covers the opening and extends laterally beyond the opening along the wall's second side 51 so as to tightly contact tissue adjacent the opening.

FIGS. 5A-B show another inventive treatment system for blocking a fistulous opening or passage that extends through a subcutaneous wall or wall-like structure. This system includes a first capping arrangement 60, a guiding member 61 and a second capping arrangement 62. First capping arrangement 60 is positioned against a first side 64 of a subcutaneous wall or wall-like structure and over a primary fistula opening in the wall. First side 64 could be a luminal surface of the stomach or other portion of the alimentary canal. Guiding member 61 is connected to the first capping arrangement for extending into other regions of the fistula when the capping arrangement is positioned over the primary fistula opening. In this illustrative scenario, the primary opening leads through the subcutaneous wall or wall-like structure and into a somewhat bulbous fistula void 65 that is defined in part by a second side 66 of the wall-like structure. This bulbous void may be a fistula tract that has widened somewhat near the primary fistula opening, or it could represent any number of other abnormalities (e.g., an abscess) in which disease, deformation, trauma, etc. has led to the existence of such a void.

Second capping arrangement 62 is received over and is translatable along guiding member 61. This particular guiding member includes retention elements 67 which are cooperable with second capping arrangement 62 for selectively retaining the second capping arrangement at a particular location along the guiding member. Second capping arrangement 62 includes a backing member 68 that is adjacent, and optionally connected to, a compressible fill material 69. The second capping arrangement can be advanced through the fistula until the compressible fill material 69 contacts tissues defining the fistula void 65 which includes the second side 66 of the subcutaneous wall-like structure. As shown in FIG. 5B, in some preferred forms, sufficient advancement can cause the fill material to become tightly compressed between the backing member 68 and these tissues, potentially forcing portions of the fill material into the primary fistula opening and into contact with the first capping arrangement 60 for enhanced blocking, closure, sealing, etc, in and/or around the primary opening. Retention elements 67 facilitate maintaining the treatment system in such a condition. Any suitable retention element or system can be employed in this regard for adjusting and maintaining the positioning of the second capping arrangement along the guiding member. Generally, the backing member will provide an opening or passageway through which the guiding member can be passed. The opening or passageway and the retention elements will be cooperatively shaped and sized so that the retention elements can be forced one-by-one through the opening or passageway in a first direction by applying a certain degree of force to the elements; however, travel of the retention elements back through the opening or passageway will be inhibited or even prevented under conditions expected at the treatment site.

FIG. 6A shows an inventive treatment system for blocking a fistulous opening or passage 70 that extends through a subcutaneous wall or wall-like structure 71. This system includes a first capping arrangement 73, a guiding member 74, a filling material 75 and a second capping arrangement 76. First capping arrangement 73 is positioned along a first side 77 of the wall-like structure 71 with the guiding member 74 extending from the first capping arrangement and through passage 70. Second capping arrangement 76 is positioned along a second side 78 of the wall-like structure and is received over guiding member 74. Filling material 75, which is not attached (at least not initially) to either of the capping arrangements, happens to be shown along the first side 77 of the wall-like structure 71 in FIG. 6A. In one illustrative treatment scenario, the opposing capping arrangements are cinched together along the guiding member and around the wall-like structure so as to force the filling material 75 into passage 70. Depending on its size, shape, materials of construction, etc., the filling material can be sufficient to substantially fill passage 70, and in some cases to also provide material residing on either side of the wall-like structure 71 with the capping arrangements helping to hold the filling material in place. FIG. 6B shows a similar embodiment except that the filling material 75 has been directly attached to the first capping arrangement 73.

FIGS. 7A-B show another inventive product that can be used to treat fistulae and other openings and passageways in the body. In this particular instance, treatment is being carried out on a subcutaneous wall through which a fistulous passage 80 has formed. The product includes a first capping arrangement 81, a guiding member 82 and a second capping arrangement 83. First capping arrangement 81 includes a backing member 84 that is attached to a compressible filling material 85, and as shown in FIG. 7A, it can be delivered to the fistula so that backing member 84 is positioned a distance from a first side 86 of the tissue wall with the filling material 85 extending from the backing member and through passage 80. The filling material 85 has a certain width at its connection to the backing member and then narrows slightly from there as it traverses passage 80 before widening significantly as it extends along a second side 87 of the tissue wall. This sort of design provides a dumbbell-shaped component in which one end of the component is backing member 84 and the opposite end of the component is provided by filling material 85. There are a variety of ways to deliver a filling material of this general shape into a passage such as passage 80. In one particularly preferred form, first capping arrangement 81 will be compactable for receipt in a delivery sheath that is capable of passing through passage 80.

FIG. 7A shows second capping arrangement 83 in the process of being advanced along guiding member 82 toward passage 80. A plurality of one-way retention elements 88, which are cooperable with the second capping arrangement, are arranged along the guiding member for selectively retaining the second capping arrangement at a particular location along the guiding member. Second capping arrangement 83 can be advanced through the fistula until it contacts filling material 85. By forcing the opposing capping arrangements toward one another around the tissue wall, filling material 85 can be compressed longitudinally between backing member 84 and second capping arrangement 83, for example, so as to compact the filling material in and around passage 80, and in some cases, to fill and substantially seal off the passage. In this regard, as shown in FIG. 7B, with backing member 84 forcefully contacting the first side 86 of the tissue wall and the back side of the filling material 85 forcefully contacting the second side 87 of the tissue wall, both ends of passage 80 can be covered and filled for enhancing closure of the passage. Retention elements 88 facilitate maintaining the treatment system in such a condition.

Figure 8:
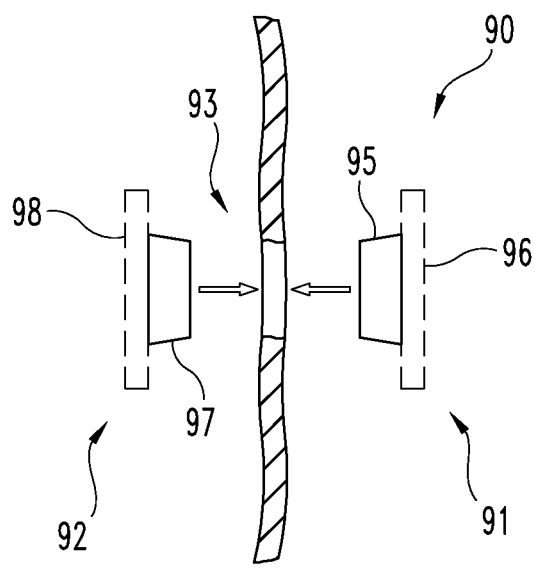
FIG. 8 shows yet another inventive medical product at a treatment site.

FIG. 8 shows components of another illustrative treatment system 90 which includes a first capping arrangement 91 and a second capping arrangement 92 where either of these capping arrangements could be incorporated into one or more of the treatment systems disclosed herein. In this particular instance, the opposing capping arrangements are being brought together around a fistula opening or passage 93 in a wall of subcutaneous tissue. Such positioning could be achieved, for example, by directly advancing either capping arrangement to the treatment site with or without use of a delivery sheath, or by advancing one or both capping arrangements along a suture or other guiding-type element, or in any other suitable fashion. First capping arrangement 91 includes a first filling material body 95 with an optional support element 96 providing support to the filling body. Second capping arrangement 92 includes a second filling material body 97 and can also incorporate an optional support element 98 as shown in phantom in FIG. 8. In an illustrative treatment scenario, the opposing filling material bodies can be forced toward one another subcutaneously in the direction of the arrows shown, with one or both filling bodies potentially entering the passage 93 and/or potentially contacting one another in and/or around the passage. Thereafter, the capping arrangements can be held in such a condition in any suitable manner, for example, by bonding or otherwise anchoring the capping arrangements to each other and/or to the subcutaneous tissue wall. Also, while not required, the filling material bodies can be tapered somewhat to facilitate their entry into passage 93.

Figure 9:
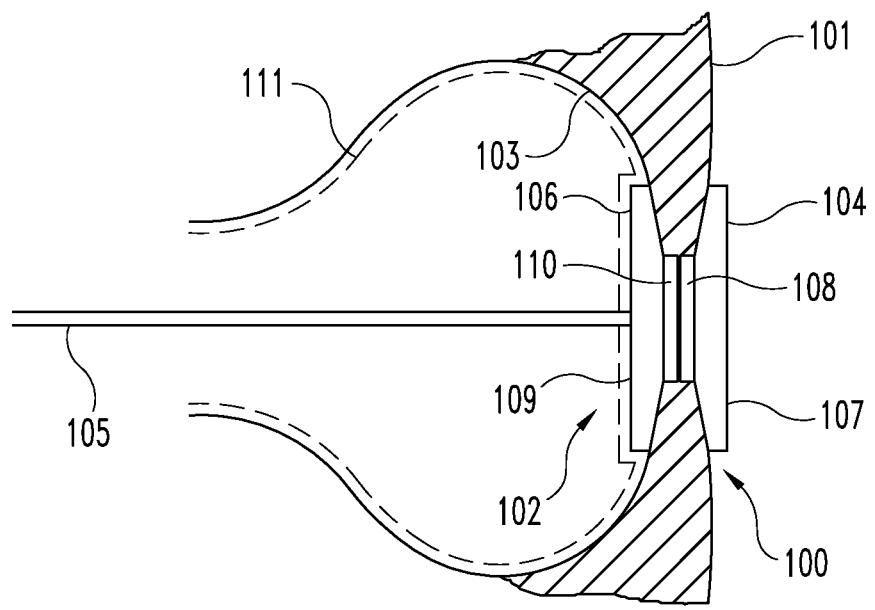
FIG. 9 shows still another inventive medical product at a treatment site.

FIG. 9 shows another illustrative treatment scenario in which an inventive system is being used to treat a fistulous passage that extends through a subcutaneous wall or wall-like structure. This particular fistulous passage has a first opening 100 that is located in a first side 101 of the wall-like structure where this first side is provided by a luminal wall of the intestines. The fistulous passage leads from first opening 100 through the wall-like structure and through a second opening 102 into a somewhat bulbous fistula void that is defined in part by a second side 103 of the wall-like structure. This system includes a first capping arrangement 104, a guiding member 105 and a second capping arrangement 106. First capping arrangement 104 is positioned against the first side 101 of the wall and over the first opening 100 with the guiding member 105 extending away from the first capping arrangement and into the fistula void. Second capping arrangement 106 is received over guiding member 105 and is positioned against the second side 103 of the wall and over the second subcutaneous opening 102. First capping arrangement 104 includes a first backing member 107 and a first filling material 108, and second capping arrangement 106 includes a second backing member 109 and a second filling material 110. Each backing member is contacting its corresponding side of the wall around an opening to the fistulous passage with the respective filling materials residing in the passage. When cinched tight, in some preferred embodiments, the respective backing members can provide good sealing against the sides of the wall around first opening 100 and second opening 102 with the filling materials contacting one another in the fistulous passage and substantially filling the passage. Thereafter, the capping arrangements can be held in such a condition in any suitable manner, for example, by bonding or otherwise anchoring the capping arrangements to each other and/or to the subcutaneous tissue wall and/or by fixing the second capping arrangement along the guiding member. Optionally, a back filling material 111 (shown in phantom in FIG. 9) such as that described in relation to FIG. 3 can be delivered into the fistula to fill the fistula void, or a portion thereof.

Figure 10:
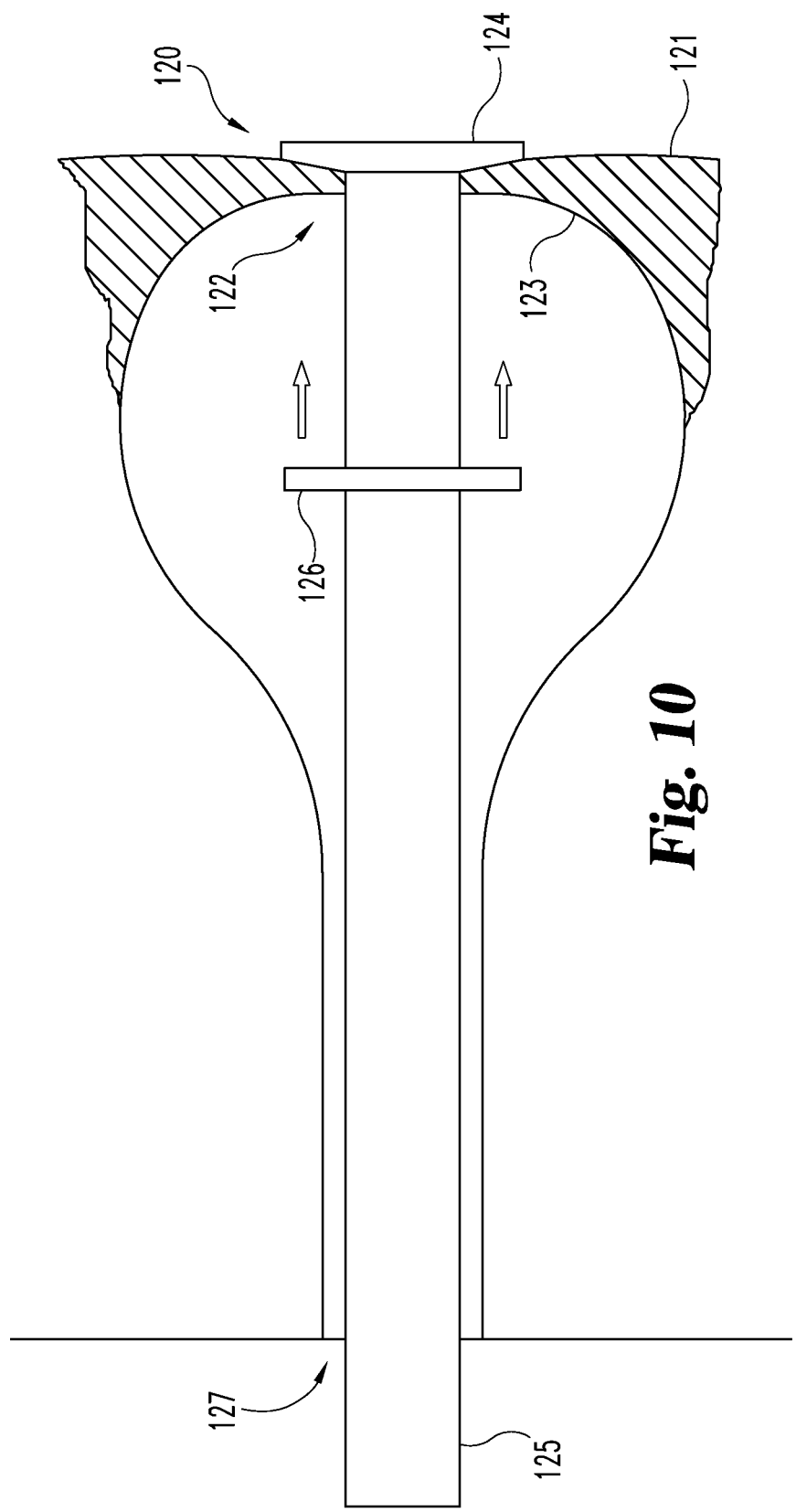
FIG. 10 shows yet another inventive medical product at a treatment site.

FIG. 10 shows another illustrative treatment scenario in which an inventive system is being used to treat a fistulous passage. This particular fistulous passage has a first opening 120 that is located in a first side 121 of a wall-like structure where this first side is provided by a luminal wall of the alimentary canal. The fistulous passage leads from first opening 120 through the wall-like structure and through a second opening 122 into a somewhat bulbous void that is defined in part by a second side 123 of the wall-like structure. This system includes a first capping arrangement 124, a guiding member 125 and a second capping arrangement 126. First capping arrangement 124 is positioned against the first side 121 of the wall and over the first opening 120 with the guiding member 125 extending away from the first capping arrangement and through the fistula where it exits the fistula through a skin-side opening 127. Guiding member 125 includes a generally cylindrical three-dimensional plug body of sufficient length to extend the length of the fistula and of sufficient width to generally fill portions of the fistula including the fistulous passage in the wall-like structure. Second capping arrangement 126 is received over this elongate plug body and is translatable therealong in the direction of the arrows shown, for example, to position the second capping arrangement against the second side 123 of the wall and over and/or around the second subcutaneous opening 122. Thereafter, the capping arrangements can be held in such a condition in any suitable manner, for example, by bonding or otherwise anchoring the capping arrangements to the wall and/or by fixing the second capping arrangement along the guiding body 125.

When a capping arrangement incorporates a frame or frame-like device, the frame can be associated with one or more of a variety of materials to form effective capping arrangements. Useful covering and other materials for capping purposes include naturally-derived and non-naturally-derived materials such as those described elsewhere herein. Both resorbable and non-resorbable materials may be employed in this regard. In some preferred embodiments, polymeric materials are associated with support structures to form useful capping members. These include synthetic and non-synthetic polymers. These various materials can be applied to or otherwise associated with support members in a variety of manners including some that involve mechanical fastening of an already-formed material, forming material along and/or around portions of the frame (e.g., in a mold or form, by spray coating, dip coating, etc.), thermoforming, solvent dissolution, and variations and combinations thereof.

Figure 11:
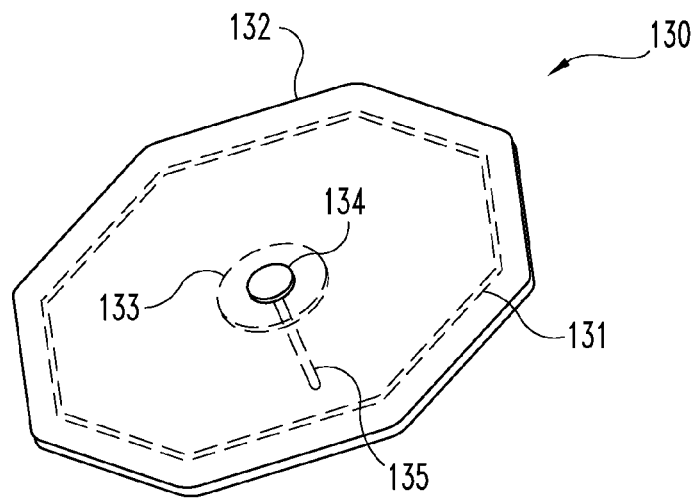
FIG. 11 shows a capping arrangement according to one embodiment of the present invention.

With reference now to FIG. 11, shown is a capping arrangement 130 according to another embodiment of the present invention. Capping arrangement 130 includes a generally octagonal, resilient wire support frame 131 that is embedded within a deformable covering material 132. An embedded frame element of this sort can be provided in a variety of manners including, for example, by casting a polymerizable, crosslinkable or otherwise hardenable flowable material onto and around all or a portion of the frame member, and then causing the flowable material to polymerize, crosslink and/or otherwise harden. In one preferred embodiment, an embedded frame element is provided by positioning a closed circumference wire frame between layers of a deformable material and then bonding the layers together to at least partially embed the frame in the material. In some cases, pieces of a somewhat flexible material are positioned around a frame, and then the material is physically, chemically and/or otherwise treated (e.g., lyophilized, heated, etc.) so that the material becomes less flexible and/or more uniform for maintaining the material in a desired configuration. In some forms, a Nitinol frame is positioned between layers of a polyurethane material such as THORALON® or a thermoplastic silicone, and then the layers are heated to thermoform the layers together around the frame. Yet, it will be understood that support frame 131 and covering material 132 can each be formed with a variety of materials as described elsewhere herein, and that the frame may be attached or otherwise associated with the covering material in any suitable fashion.

In this specific illustrative embodiment, capping arrangement 130 additionally includes a washer 133 that is positioned to the interior of support frame 131 and that is also embedded within covering material 132 although it could be associated with the covering material in other non-embedded ways. A connecting pin that includes a head portion 134 and a shank portion 135 is associated with the other capping elements, for example, where the shank of the connecting pin is received through a center hole in washer 133 as shown in FIG. 11. Preferably but not necessarily, washer 133 is formed with a material such as stainless steel that can be non-invasively visualized, thus making both washer 133 and support frame 131 imageable in this way. While the relative dimensions of the various capping components shown in FIG. 11 are advantageous in certain embodiments of the invention, it will be understood that these dimensions can be varied as desired to suit a particular application, patient, etc.

Figure 12:
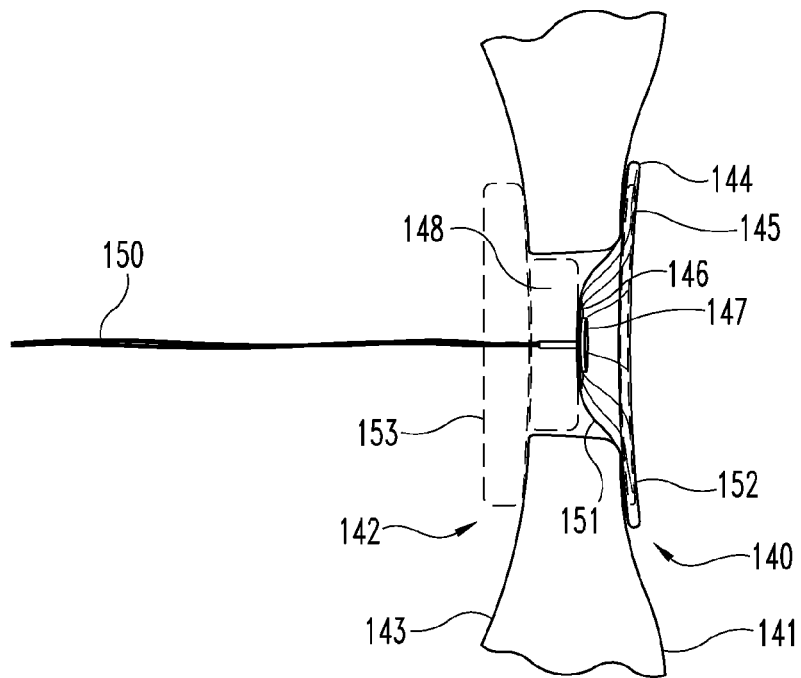
FIG. 12 shows an inventive medical product at a treatment site.

FIG. 12 shows another illustrative treatment scenario in which an inventive system is being used to treat a fistulous passage that extends through a subcutaneous wall or wall-like structure. This particular fistulous passage has a first opening 140 that is located in a first side 141 of the wall-like structure where this first side is provided by a luminal wall of the intestines. The fistulous passage leads from first opening 140 through the wall-like structure and through a second opening 142 into a fistula void that is defined in part by a second side 143 of the wall-like structure. This system includes a first capping arrangement that is similar to that shown in FIG. 11. In particular, the first capping arrangement includes a deformable covering material 144, a polygonal wire frame member 145 embedded in the covering material, a washer 146 embedded in the covering material to the interior of the polygonal frame member, and a connecting pin 147 with a shank extending through the covering material and the embedded washer. This particular capping arrangement further includes an optional filling material 148 (shown in phantom) which can reside in and/or around the fistula as shown, for example, where the filling material is attached to the covering material with the shank of the connecting pin extending through the filling material. Alternatively, such a filling material, independent of the first capping arrangement, could be threaded along the suture line to the treatment site. The connecting pin is connected to suture line 150 so that when the first capping arrangement is positioned against the first side 141 of the wall and over the first opening 140, the suture line 150 can extend away from the first capping arrangement and into the fistula void.

With such designs, a pulling element such as suture line 150 can be pulled through the fistula (e.g., generally away from the primary fistula opening) so that some portions of the first capping arrangement will be pulled into the fistula (e.g., become internalized within the fistula) while other portions of the first capping arrangement will remain outside the fistula for enhancing closure of the primary fistula opening. For example, as shown in this specific illustrative embodiment, this sort of action can draw washer 146 and interior regions 151 of the deformable covering material into the fistula through the primary opening with the polygonal support frame 145 and peripheral regions 152 of the deformable covering material (e.g., including material immediately proximate the support frame) remaining external of the fistula. Desirably, a support member such as support frame 145 will be sized and configured so that it remains generally outside the fistula (e.g., along luminal surfaces of the intestinal wall in areas of the wall extending somewhat beyond the primary fistula opening) even when a considerable amount of pulling force is applied to a pulling element such as suture line 150. Interior regions 151 of the covering material, which are now located in the fistula, include material that previously (i.e., prior to deformation) resided outside of the fistula. Such peripheral regions of the covering material can, in some instances, promote and/or facilitate a better blockage or exclusion of the fistula from the intestinal canal, and in some instances, will contribute to sealing off of the primary fistula opening from the contents of the intestines.

In some forms, the first capping arrangement is made to deform so that portions of the covering material very snugly conform to patient tissue at the primary fistula opening in a generally non-planar condition such as a cupping or cup-like arrangement. As suture line 150 is pulled through the fistula, washer 146 moves away from support frame 145 in that same direction. Because support frame 145 and washer 146 are both formed with non-invasively imageable materials, when viewed from a vantage point corresponding to, for example, that shown in FIG. 12, it is possible to determine the relative positioning of the two components in the body as suture line 150 is pulled. This may be helpful, for example, to determine when a desired amount of deformation of the covering material has been achieved, for example, in an effort to try to seal off the primary fistula opening in instances where such sealing off can be achieved. When it can be visualized that the support frame and washer are desirably spaced or off-set from one another, sufficient tension can be maintained on the suture line 150 to retain the conforming condition of the deformable covering material. The desired amount of off-set can vary depending perhaps on the materials of construction of the grafting device, size of the fistula or other body passage being treated, etc.

An optional second capping arrangement 153 (shown in phantom) can be received over suture line 150, for example, to be positioned against the second side 143 of the wall and over the second subcutaneous opening 142 as shown in FIG. 12. Second capping arrangement 153 can have any suitable design, for example, including a backing member and/or a filling material as described in some of the other disclosed embodiments. When first and second capping arrangements are utilized, each one can contact its corresponding side of the subcutaneous wall and be positioned over first opening 140 and second opening 142, respectively. Thereafter, the capping arrangements can be held in such a condition in any suitable manner, for example, by bonding or otherwise anchoring the capping arrangements to each other and/or to the subcutaneous tissue wall and/or by fixing the second capping arrangement along the guiding member.

Turning now to a more detailed discussion of materials that can be utilized in the present invention, as discussed elsewhere herein, any part of an inventive construct can be formed with or include naturally derived and/or non-naturally derived materials. In this regard, one or more components of an inventive construct may comprise one or more of a variety of synthetic polymeric materials including but not limited to bioresorbable and/or non-bioresorbable plastics. Bioresorbable, or bioabsorbable polymers that may be used include, but are not limited to, poly(L-lactic acid), poly-caprolactone, poly(lactide-co-glycolide), poly(hydroxybutyrate), poly(hydroxybutyrate-co-valerate), polydioxanone, polyorthoester, polyanhydride, poly(glycolic acid), poly(D, L-lactic acid), poly(glycolic acid-co-trimethylene carbonate), polyhydroxyalkanaates, polyphosphoester, polyphosphoester urethane, poly(amino acids), cyanoacrylates, poly (trimethylene carbonate), poly(iminocarbonate), copoly (ether-esters) (e.g., PEO/PLA), polyalkylene oxalates, and polyphosphazenes. These or other bioresorbable materials may be used, for example, where only a temporary function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

As well, inventive constructs, or any component thereof, can incorporate biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Any part of an inventive construct can be formed with or include a remodelable material. Particular advantage can be provided by devices that incorporate a remodelable collagenous material. Such remodelable collagenous materials, whether reconstituted or naturally-derived, can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth on, around, and/or in bodily regions in which inventive devices are implanted or engrafted.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Remodelable ECM tissue materials harvested as intact sheets from a mammalian source and processed to remove cellular debris advantageously retain at least a portion of and potentially all of the native collagen microarchitecture of the source extracellular matrix. This matrix of collagen fibers provides a scaffold to facilitate and support tissue ingrowth, particularly in bioactive ECM implant materials, such as porcine small intestinal submucosa or SIS (Surgisis® Biodesign™, Cook Medical, Bloomington Ind.), that are processed to retain an effective level of growth factors and other bioactive constituents from the source tissue. In this regard, when an inventive construct incorporates this sort of material, cells will invade the remodelable material upon implantation eventually leading to the generation of a newly-remodeled, functional tissue structure in the patient.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa-containing or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Turning now to a discussion of three-dimensionally stable materials that can be incorporated into inventive grafts, and components thereof, in accordance with some aspects of the present invention, such materials may include any suitable biocompatible sponge or foam material. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers. More preferred sponge compositions of the invention will comprise collagen as a matrix-forming material, either alone or in combination with one or more other matrix forming materials. In general, sponge matrices useful in embodiments of the invention can be formed by providing a liquid solution or suspension of a matrix-forming material, and causing the material to form a porous three-dimensionally stable structure; however, a sponge or foam material can be formed using any suitable formation method, as is known in the art.

Preferred sources of collagen for forming collagen-containing sponge matrices include extracellular matrix materials as discussed above, such as collagenous submucosal tissues, and other collagenous basement membrane materials. These include, for example, small intestinal submucosa, stomach submucosa, urinary bladder submucosa, liver basement membrane, and other basement membrane materials. For additional information as to these collagenous matrix materials and their preparation, reference can be made for example to U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety. In forming sponge matrices, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

Sponge matrix materials can be highly expandable when wetted, so as to achieve an expanded configuration. Illustratively, expandable sponge materials can exhibit the capacity to expand at least 100% by volume, more preferably at least about 200% by volume, and typically in the range of about 300% by volume to about 1000% by volume, when wetted to saturation with deionized water. Sponge materials used in the invention can also exhibit advantageous rates of expansion, achieving volume expansions as noted above in less than about 10 seconds, more preferably less than about 5 seconds, when immersed in deionized water.

In additional embodiments, a graft element useful in the invention can be made from ECM's or other collagenous materials that have been subjected to processes that expand the materials. Suitable collagenous or ECM materials can be prepared, for example, as described in U.S. Patent Publication No. 20090326577 (Cook Biotech Incorporated) published Dec. 31, 2009, which is hereby incorporated by reference in its entirety. When used in the invention, expanded remodelable collagenous materials can be provided in any suitable form, including a flowable aqueous composition (e.g., a fluidized composition), a powder, a gel, a sponge, foam, one or more sheets, or a cast body. In one embodiment, the expanded remodelable collagenous material is processed into a fluidized composition, for instance using techniques as described in U.S. Pat. No. 5,275,826.

In certain forms, such expanded materials can be formed by the controlled contact of an ECM material with one or more alkaline substances until the material expands, and the isolation of the expanded material. Any suitable alkaline substance generally known in the art can be used in this regard. Suitable alkaline substances can include, for example, salts or other compounds that that provide hydroxide ions in an aqueous medium. Preferably, the alkaline substance comprises sodium hydroxide (NaOH). Illustratively, the contacting with an alkaline substance can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device, for example, so as to become anchored within a patient or otherwise occupy a space within a patient such as when closing or filling an opening or passageway in the patient.

Expanded collagenous or ECM materials can be formed by the controlled contact of a collagenous or ECM material with an aqueous solution or other medium containing sodium hydroxide. Notably, such treatment can be used to promote substantial expansion (i.e., greater than about 20% expansion). In accordance with certain aspects of the invention, this expanded material is processed into a variety of useful medical materials and devices. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. It will be apparent to one skilled in the art that the magnitude of the expansion is related to several factors, including for instance the concentration or pH of the alkaline medium, the exposure time of the alkaline medium to the material, and temperature used in the treatment of the material to be expanded, among others. These factors can be varied through routine experimentation to achieve a material having the desired level of expansion, given the disclosures herein.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of sponge or foam shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans. Accordingly, the treatment of a remodelable collagenous material with an alkaline substance as described herein can cause the material to expand to at least about twice its original volume, can alter the surface and/or porosity characteristics of the material, and can deplete the material of certain bioactive components. In some embodiments, this is accomplished while maintaining the material as an intact collagenous sheet, wherein the sheet can be further processed into any of a variety of medical materials and/or devices. Further, the remodelable collagenous material, such as an ECM sheet, can be treated with the alkaline medium so as to expand it as described herein, while the material retains an amount of a growth factor such as FGF-2, or another bioactive component such as fibronectin and/or heparin, that is/are native to the source tissue for the ECM or other collagenous material.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression.

Products and methods of the invention can be used to treat a variety of fistulae and other passages and openings in the body. In some preferred aspects, products and methods are adapted for treating fistulae having at least a primary opening and a fistula tract extending therefrom, for example, a primary opening in the alimentary canal. In this regard, inventive products and methods may be useful to treat urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae. Inventive products and methods can be used to treat a fistula regardless of its size and shape.

Additionally, inventive products and methods can be used to occlude, block, fill, plug and/or otherwise treat a variety of vascular (e.g., arterial, venous, etc.) and non-vascular openings and passageways in the body. In some instances, an inventive device will be configured for placement in a naturally occurring location in the body, for example, in a native lumen or other open space in a bodily system, e.g., in an organ or other component of the circulatory, respiratory, digestive, urinary and reproductive, sensory, or endocrine systems. In certain aspects, a space to be occupied by an inventive graft is one that exists naturally in the body but relates to a disease, defect, deformation, etc. Alternatively, an opening or passageway to be occupied might be one resulting from an intentional or unintentional trauma to the body including but not limited to some relating to vehicular accidents, gunshots and other similar wounds, etc., as well as some resulting from the passage of a medical instrument (e.g., a needle, trocar, etc.) through cutaneous, subcutaneous, and/or intracutaneous tissue.

The present invention also provides, in certain aspects, a line of medical products, wherein a medical product of the invention includes one or more devices, apparatuses or systems of the invention in a sealed package. In some forms of the invention, medical products are provided that include one or more inventive devices or systems enclosed within sterile medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A medical product for treating a fistulous passage that extends through a subcutaneous wall structure, the subcutaneous wall structure including a wall of the alimentary canal and having a first side that is provided by the luminal side of the alimentary canal wall and a second subcutaneous side that is opposite said first side, wherein the fistulous passage extends from a primary opening in the subcutaneous wall structure to a secondary opening in the skin, the medical product comprising:
   a first capping arrangement deliverable to the first side of the subcutaneous wall structure and positionable over the primary opening on the first side of the subcutaneous wall structure said first capping arrangement comprising a first filling material configured to extend into the fistulous passage;
   a guiding member extending from the first capping arrangement and extendable through the fistulous passage and through the secondary opening in the skin when the first capping arrangement is positioned over the primary opening on the first side of the subcutaneous wall structure; and
   a second capping arrangement received on and deliverable along the guiding member to the second side of the subcutaneous wall structure when the first capping arrangement is positioned over the primary opening on the first side of the subcutaneous wall structure, said second capping arrangement sized and configured for passage through the secondary opening and along the fistulous passage to the primary opening, wherein the second capping arrangement is positionable within the fistula tract over the primary opening on the second side of the subcutaneous wall structure, said second capping arrangement comprising a second filling material.

2. The medical product of claim 1, wherein at least one of the first filling material and the second filling material comprises a remodelable material.

3. The medical product of claim 1, wherein at least one of the first filling material and the second filling material comprises an extracellular matrix material.

4. The medical product of claim 1, wherein at least one of the first filling material and the second filling material comprises a sponge form material.

5. The medical product of claim 1, wherein said guiding member comprises a suture.

6. The medical product of claim 1, wherein said guiding member comprises an elongate three-dimensional plug body.

7. The medical product of claim 1, wherein said guiding member and said second capping arrangement are cooperable with one another for generally maintaining a position of the second capping arrangement along the guiding member.

8. The medical product of claim 1, wherein the first capping arrangement is compactable for delivery to the first side of the subcutaneous wall structure through the fistulous passage.

9. A medical product for treating a fistula having a primary opening in a wall of the alimentary canal and a secondary fistula opening in the skin, said primary opening having a first side on the luminal side of the wall and a second side at or near the abluminal side of the wall, and wherein the second side of the primary opening occurs at a subcutaneous location within the fistula, the medical product comprising:
   a first capping arrangement deliverable to the alimentary canal and positionable over the first side of the primary fistula opening said first capping arrangement comprising a first filling material configured to extend into the primary opening;
   a guiding member extending from the first capping arrangement and extendable through the fistula tract and out of the secondary fistula opening when the first capping arrangement is positioned over the first side of the primary fistula opening;
   a second capping arrangement received on said guiding member and deliverable through the fistula along the guiding member, the second capping arrangement deliverable through the secondary fistula opening and toward the first capping arrangement when the first capping arrangement is positioned over the first side of the primary fistula opening, and wherein said second capping arrangement is positionable over the second side of the primary fistula opening, said second capping arrangement comprising a second filling material.

10. The medical product of claim 9, wherein said first filling material and said second filling material are sized and configured for contacting one another within the fistula proximate the primary fistula opening.

11. A method for treating a fistula having a primary opening in a wall of the alimentary canal and a secondary fistula opening in the skin, said primary opening having a first side on the luminal side of the wall and a second side at or near the abluminal side of the wall, and wherein the second side of the primary opening occurs at a subcutaneous location within the fistula, the method comprising:

delivering a first capping arrangement to the alimentary canal such that the first capping arrangement is positioned over the first side of the primary fistula opening and provides a first filling material within the fistula;

providing a guiding member extending from the first capping arrangement and through the fistula toward the secondary fistula opening when the first capping arrangement is positioned over the primary fistula opening; and delivering a second capping arrangement through the secondary fistula opening and along the guiding member so that the second capping arrangement advances through the fistula toward the first capping arrangement when the first capping arrangement is positioned over the first side of the primary fistula opening; and positioning the second capping arrangement such that the second capping arrangement is positioned subcutaneously within the fistula tract and over the second side of the primary opening.

12. The method of claim 11, wherein delivering the first capping arrangement to the alimentary canal includes passing the first capping arrangement through the fistula in a direction from the secondary fistula opening to the primary opening.

13. The method of claim 11, wherein said second capping arrangement is delivered through the secondary fistula opening while received over said guiding member.

14. The method of claim 11, wherein advancing the second capping arrangement through the fistula brings the second capping arrangement into contact with the first filling material.

15. The method of claim 14, wherein bringing the second capping arrangement into contact with the first filling material is effective to compress the first filling material.

16. The method of claim 11, wherein advancing the second capping arrangement through the fistula is effective to move a second filling material through the fistula toward the first filling material.

17. The method of claim 11, wherein said second capping arrangement includes a second filling material, and wherein advancing the second capping arrangement through the fistula is effective to bring the second filling material into contact with the first filling material in the fistula.

18. The method of claim 17 which includes compressing the first filling material and the second filling material together proximate the primary opening.

19. A medical product for treating a fistula having a primary opening in a wall of the alimentary canal and a secondary fistula opening in the skin, the medical product comprising:

a first capping arrangement that includes a first support element and a first filling material, said first capping arrangement deliverable to the alimentary canal for positioning over the primary fistula opening with said first support element supporting said first filling material in a blocking position over the primary fistula opening;

a guiding member extending from the first capping arrangement and extendable through the fistula toward the secondary fistula opening when said first capping arrangement is positioned over the primary fistula opening; and a second capping arrangement that includes a second support element and a second filling material, the second capping arrangement received on and deliverable along said guiding member and through the secondary fistula opening toward said first capping arrangement when said first capping arrangement is positioned over the primary fistula opening, and wherein said second capping arrangement is positionable over the primary fistula opening within the fistula tract.

20. The medical product of claim 19, wherein said first support element comprises a resilient wire support frame supporting a deformable covering material.

21. The medical product of claim 20, wherein said first filling material is connected to said deformable covering material.

22. The medical product of claim 19, wherein said first capping arrangement is capable of generally sealing off the primary opening.

23. A method for treating a fistulous passage that extends through a subcutaneous wall structure, the subcutaneous wall structure including a wall of the alimentary canal and having a first side that is provided by the luminal side of the alimentary canal wall and a second subcutaneous side that is opposite said first side, wherein the fistulous passage extends from an opening in the first side of the subcutaneous wall structure to an opening in the second side of the subcutaneous wall structure, the method comprising:

deploying a first capping arrangement to the alimentary canal in a blocking position over the opening in the first side of the subcutaneous wall structure; and deploying a second capping arrangement in a subcutaneous blocking position over the opening in the second side of the subcutaneous wall structure.

24. The method of claim 23, further comprising compressing the subcutaneous wall structure between said first capping arrangement and said second capping arrangement.

25. The method of claim 23, wherein said first capping arrangement includes a guiding member, and wherein deployment of the first capping arrangement and the second capping arrangement leaves the guiding member extending through the fistulous passage and through the opening in the second side of the subcutaneous wall structure with the second capping arrangement received over the guiding member.

26. The method of claim 25, further comprising generally fixing said second capping arrangement in position along the guiding member.

27. The method of claim 26, which includes the subcutaneous wall structure being squeezed between the second capping arrangement and the first capping arrangement.

28. The method of claim 23, further comprising positioning a fill material between the first capping arrangement and the second capping arrangement.

29. The method of claim 28, wherein said first capping arrangement or said second capping arrangement provides said fill material.

* * * * *